United States Patent
Hirano et al.

(10) Patent No.: US 7,952,072 B2
(45) Date of Patent: May 31, 2011

(54) TEST APPARATUS

(75) Inventors: Katsunori Hirano, Yokohama (JP); Tadanobu Toba, Yokohama (JP); Masahiro Ohashi, Hitachinaka (JP); Masashi Wada, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 387 days.

(21) Appl. No.: 12/173,038

(22) Filed: Jul. 15, 2008

(65) Prior Publication Data

US 2009/0072138 A1    Mar. 19, 2009

(30) Foreign Application Priority Data

Sep. 13, 2007   (JP) .................. 2007-237988

(51) Int. Cl.
*H01J 37/304*   (2006.01)
(52) U.S. Cl. ...................................... 250/310
(58) Field of Classification Search .............. 250/310
See application file for complete search history.

(56) References Cited

U.S. PATENT DOCUMENTS 4,870,344 A * 9/1989 Stille ............... 250/310

FOREIGN PATENT DOCUMENTS

JP    2003-142019    5/2003

* cited by examiner

*Primary Examiner* — Kiet T Nguyen
(74) *Attorney, Agent, or Firm* — Antonelli, Terry, Stout & Kraus, LLP.

(57) ABSTRACT

A scan control unit for generating two-dimensional coordinates for performing a scan with an electron beam of an electron scanning microscope is provided with first and second transforming units for transforming coordinates in the horizontal (X) direction and the vertical (V) direction. An area to be tested in a sample is scanned with an electron beam in an arbitrary direction. As the first and second transforming units, small-capacity transformation tables (LUTs) capable of operating at high speed in each of the horizontal (X) direction and the vertical (Y) direction are used. By also using a large-capacity transformation table (LUT) that stores coordinate transformation data corresponding to plural scan types, a test apparatus compatible with the plural scan types, having multiple functions, and capable of performing high-speed scan control is realized.

15 Claims, 10 Drawing Sheets

SCAN BOTH X AND Y COORDINATES IN ORDER

FIG.5B

SCAN X COORDINATES IN ORDER AND SCAN Y COORDINATES EVERY ONE OR MORE COORDINATES

TEST APPARATUS

CLAIM OF PRIORITY

The present application claims priority from Japanese patent application JP 2007-237988 filed on Sep. 13, 2007, the content of which is hereby incorporated by reference into this application.

BACKGROUND OF THE INVENTION

The present invention relates to a test apparatus for testing a semiconductor device, a substrate, a photomask (exposure mask), a liquid crystal, and the like having a fine pattern.

In recent years, as semiconductor integrated circuits are becoming finer and having higher integration, a pattern on semiconductor wafer is tested at the end of each of manufacturing processes of the semiconductor integrated circuits in order to detect, early or in advance, occurrence of an abnormality and a failure in the manufacturing processes. Test methods and apparatuses to detect a defect are being practically used. In the test apparatuses, a test is conducted by obtaining image information of an area to be tested with a scanning electron microscope (hereinbelow, abbreviated as SEM) using the electron beam technique.

Also in the control of the dimensions of a process pattern in the manufacture of a semiconductor integrated circuit, a critical-dimension SEM (called CD-SEM) as an SEM using the electron beam technique dedicated to semiconductors is used. The CD-SEM is used for observation of a process pattern and high-precision dimension measurement.

Also in the control of the yield and the like of a semiconductor integrated circuit, to detect a defect in a device pattern of a chip by an SEM using the electron beam technique, for example, a test apparatus such as a defect review SEM (DR-SEM) is used.

In the apparatuses each using an SEM, an electron beam is emitted with a predetermined accelerating voltage along plural scan lines to scan an area to be tested on a semiconductor wafer. Secondary electrons generated are detected to obtain image information of the area to be tested. On the basis of the obtained image information, the area to be tested is tested. In association with increase in the diameter of a semiconductor wafer and decrease in the size of a circuit pattern in recent years, higher throughput of an apparatus is being demanded. To realize higher throughput, it is necessary to increase the speed of a scan control for performing a scan with an electron beam and an imaging process for computing obtained image information.

On the other hand, a test apparatus that obtains an image by using an electron beam has a problem of the influence of a charge-up phenomenon. It is becoming difficult to obtain high-precision image information. The charge-up phenomenon is a phenomenon that, in the case of irradiating a sample with an electron beam, electrons which are incident on the sample lose their energy and are absorbed in the sample. When the sample is a conductive material, the electrons flow to a sample stage. In the case where the sample is a non-conductive sample, the electrons remain in the sample and charging occurs.

When charging occurs, the electron beam is bent due to repulsion of the charges remained at the time of emitting the electron beam to the sample and is deviated from an intended irradiation position. As a result, an obtained image is distorted. Since the generation amount of the secondary electrons changes due to the charging, a so-called potential contrast occurs such that an obtained image becomes partly light or dark due to variation in the secondary electron detection efficiency and disturbance of the track of the secondary electrons.

There are some methods to prevent the charging. Japanese Unexamined Patent Application Publication No. 2003-142019 discloses a technique of using two accelerating voltages at the time of emitting an electron beam. By irradiating at least scan lines with an electron beam at the second accelerating voltage prior to acquisition of an image of the scan lines, generation of secondary electrons is facilitated. In this case, there is the possibility that the area to be tested is unnaturally charged. In addition, since two accelerating voltages are used, the control in the apparatus becomes complicated, and there is consequently a problem that the apparatus is expensive.

SUMMARY OF THE INVENTION

In association with increase in the diameter of a semiconductor wafer and decrease in the size of a circuit pattern in recent years, higher throughput of an apparatus is being demanded. As described above, to realize higher throughput, it is necessary to increase the speed of a scan control for performing a scan with an electron beam and an imaging process for computing obtained image information. A test apparatus that obtains an image by using an electron beam has a problem of the influence of a charge-up phenomenon. It is necessary to address the charge-up phenomenon.

The present invention is directed to realize higher throughput of a test apparatus using an electron beam and to provide a test apparatus using a scan type adapted to a charging control.

The present invention provides a test apparatus in which a two-dimensional coordinate generating unit for performing a scan with an electronic beam has X and Y coordinate transforming units for transforming coordinates in each of a horizontal (X) direction an a vertical (Y) direction to obtain scan coordinates, and an area to be tested is scanned with an electron beam in an arbitrary direction.

The present invention also provides a test apparatus using an electron beam in which the scan control unit as a coordinate generating unit for generating scan coordinates has a transformation table (lookup table, hereinbelow, abbreviated as LUT) for transforming X and Y coordinates as a reference to arbitrary scan coordinates and each of the X and Y coordinates is transformed, thereby performing a scan with an electron beam in an arbitrary direction.

The present invention further provides a test apparatus using an electron beam, in which the scan control unit has a small-capacity transformation table (LUT) having a capacity equivalent to image size and transforming the X and Y scan coordinates, and a transformation table (LUT) as a storage of a large capacity which is equal to that of plural image sizes and which stores transformation data by scan types to address plural scan types. During a scan operation, coordinate transformation is performed at high speed using the small-capacity transformation table. During a scan stops, the transformation data is transferred from the large-capacity transformation table (LUT) to the small-capacity transformation table (LUT). Consequently, the test apparatus is compatible with the plural scan types, can transform coordinates to arbitrary coordinates, and can perform a high-speed scan control.

The present invention further provides a test apparatus using an electron beam, in which the scan control unit has, as the small-capacity transformation table (LUT), two or more first small-capacity transformation tables (LUTs) and two or more second small-capacity transformation tables (LUTs) for X and Y coordinates. During a scan operation, coordinate transformation is performed with the first small-capacity transformation tables (LUTs) and, simultaneously, the transformation data is transferred from the large-capacity transformation table (LUT) to the second small-capacity transformation tables (LUTs). After completion of the scan, input/output signals of the first small-capacity transformation tables (LUTs) and those of the second small-capacity transformation tables are switched, and the two or more small-capacity transformation tables (LUT) are alternately used per scan. In such a manner, transformation data for the next scan is transferred from the large-capacity transformation table to the small-capacity transformation table. By reduction in transfer time, the throughput is improved.

The present invention further provides a test apparatus using an electron beam, further including a sorting unit that sorts image data scanned in an arbitrary direction to an order of a scan in a normal predetermined direction on the basis of the scan coordinates generated by the scan control unit. The sorting unit has a sorting memory having a capacity equal to that of image data, a memory control unit for writing data to the sorting memory using the scan coordinates as a memory address, and an image range detecting unit for detecting an image computation range from the scan coordinates. The sorting unit transfers the image data to the image computing unit per image computation range, thereby performing high-speed sorting and transfer.

These and other objects, features and advantages of the invention will be apparent from the following more particular description of preferred embodiments of the invention, as illustrated in the accompanying drawings.

DESCRIPTION OF THE PREFERRED EMBODIMENTS

Prior to describing the best modes for carrying out the invention with reference to the drawings, a scan control method of the present invention and a basic configuration of an image processing system and a test apparatus using the method will be described with reference to FIG. 1.

Figure 1:
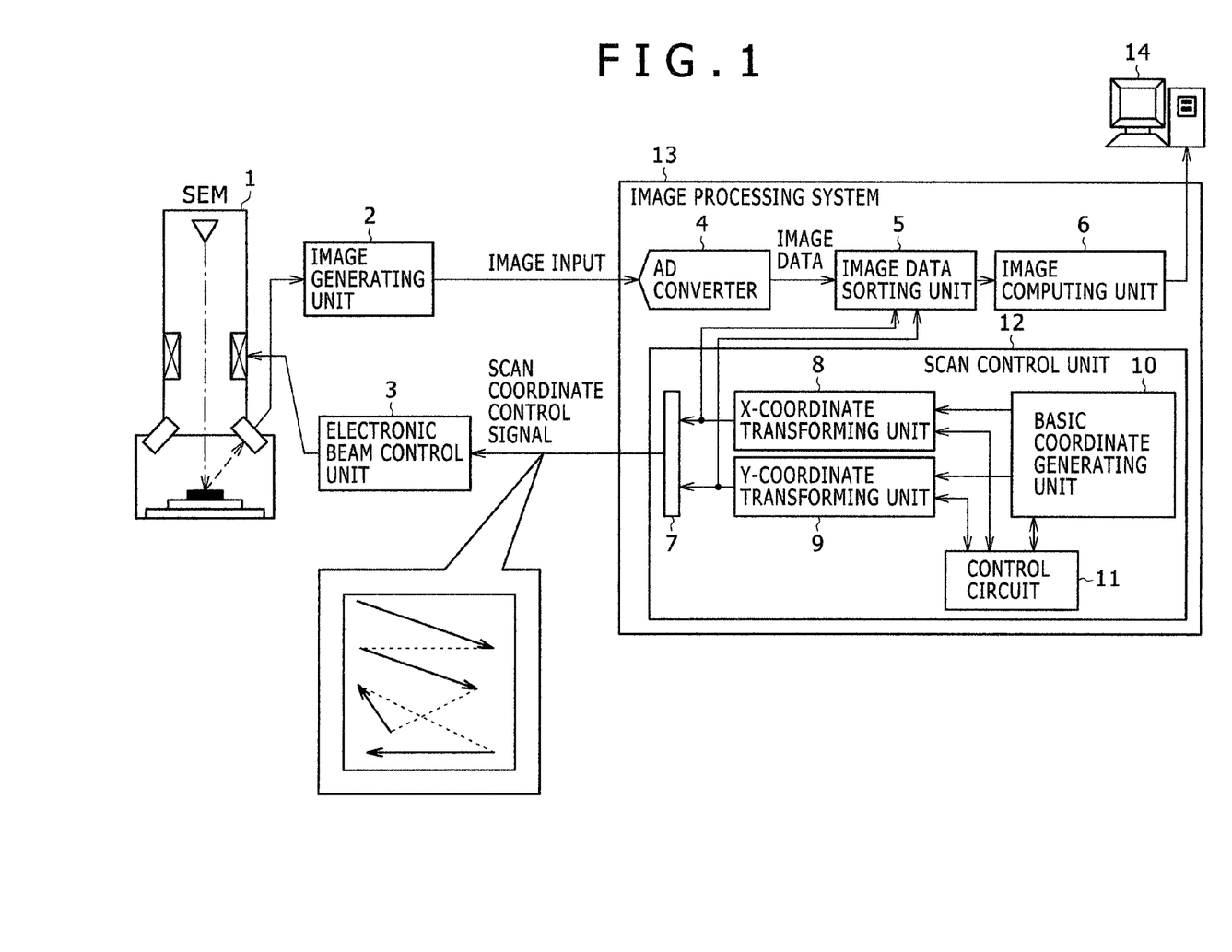
FIG. 1 is a diagram showing a basic configuration of a test apparatus using an electron beam according to the present invention.

In FIG. 1, a test apparatus using an electron beam is constructed by an SEM 1, an image generating unit 2, an electronic beam control unit 3, an image processing system 13, and an overall control unit 14 such as a personal computer (hereinbelow, abbreviated as PC) having a display as a display unit. The image processing system 13 has an AD converter 4, an image data sorting unit 5, an image computing unit 6, and a scan control unit 12. The scan control unit 12 functioning as a coordinate generating unit for generating scan coordinates is constructed by an output unit 7, an X-coordinate transforming unit 8, a Y-coordinate transforming unit 9, a basic coordinate generating unit 10, and a control circuit 11. The SEM 1 includes an electron gun for emitting an electron beam, a scan coil for controlling an irradiation position of the electron beam emitted from the electron gun, an objective lens for controlling a beam diameter by controlling the focal point of the electron beam, and a secondary electron detector for detecting secondary electrons released from a sample irradiated with the electron beam. Since the configuration of the SEM 1 is general one, it will not be described. To detect an abnormality or occurrence of a failure in a manufacturing process of the semiconductor integrated circuit early or in advance, a test is conducted using a test apparatus at the end of each of manufacturing processes. As a test method, image information of an area to be tested is acquired by scanning a sample with an electron beam along plural lines.

The image information is acquired in a unit capable of performing a process by the test apparatus. For example, in the case of testing a wafer of a semiconductor integrated circuit, an image of the whole wafer cannot be acquired at a time. Consequently, the wafer is divided by image size of 512×512 or the like and an image is acquired. The size of each of the divided pieces is used as one unit, and the range, that is, the area to be tested is scanned with an electron beam, and an image is acquired. A reference point on the division unit basis is scanned by moving a stage (a part on which the sample to be tested is mounted) in the SEM. As the semiconductor integrated circuit to be tested becomes finer, the image size increases from 512×512 to 4,096×4,096.

A scan performed in one image size as the divided unit will be described below.

First, X·Y coordinates (data) as the basis of the size of an image to be acquired are generated by the basic coordinate generating unit 10 of the scan control unit 12. For example, when the image size is 512×512, the basic coordinates (data) are generated by setting the Y coordinate to 0 and changing the X coordinate from 0 to 511 in order. Next, data is generated by setting Y to 1 and changing the X coordinate from 0 to 511 in order. The operation is repeated and coordinates are generated until the Y coordinate becomes 511. Usually, the basic coordinates (data) are used as they are. Scan coordinates are input to the electronic beam control unit 3 to perform a scan with an electron beam. In the case of performing a scan in an arbitrary direction, the basic coordinates are converted to X·Y coordinates for an arbitrary scan by using the X-coordinate transforming unit 8 and the Y-coordinate transforming unit 9. A scan coordinate control signal is input to the electronic beam control unit 3 via the output unit 7 to perform a scan with the electron beam. A scan in an arbitrary direction may be called a flat scan. An example of the flat scan of making the output unit 7 of the image processing system 13 perform a scan in an arbitrary direction is schematically shown.

In the SEM 1, an electron beam is emitted to a sample such as a semiconductor wafer on the basis of the scan coordinate control signal from the electronic beam control unit 3, secondary electrons released from the sample are detected, and a detection signal is output to the image generating unit 2. The image generating unit 2 converts the detection signal to an image signal as image information and inputs the image signal to the image processing system 13. In the image processing system 13, since the input image signal is an analog signal, the image signal is converted to a digital signal by the AD converter 4, and the digital signal as image data is obtained.

The image data as converted image information is sorted by the image data sorting unit 5. Since it is unnecessary to sort input image data in a normal scan, the image data is output as it is to the image computing unit 6. However, in the case of performing a scan in an arbitrary direction (flat scan), image data is sorted in a normal order on the basis of the scan coordinates generated by the scan control unit 12. The image sorting method will be described later. The image computing unit 6 computes the input image data, performs an image process, and transfers the processed data to the overall control unit 14. The overall control unit 14 displays the processed image data on the screen of the display as the display unit, and conducts a test on the basis of the acquired image information such as detection of an abnormality and occurrence of a failure, measurement of dimensions of a process pattern, and the like.

As obvious from the basic configuration of the present invention as described above, by providing the scan control unit 12 with the X-coordinate transforming unit 8 and the Y-coordinate transforming unit 9, a scan can be performed with an electron beam in an arbitrary direction (flat scan). By performing the scan in the arbitrary direction, charging can be prevented.

As described above, when the charging phenomenon occurs, a bending occurs due to repulsion of charges generated when the sample is irradiated with the electron beam, so that the electron beam is deviated from the inherent irradiation position. As a result, the obtained image is distorted. With the basic configuration of the invention, the sample is scanned (flat-scanned) with the electron beam in the arbitrary direction, thereby suppressing the influence of charging and enabling distortion of the acquired image to be reduced.

First Embodiment

Figure 2:
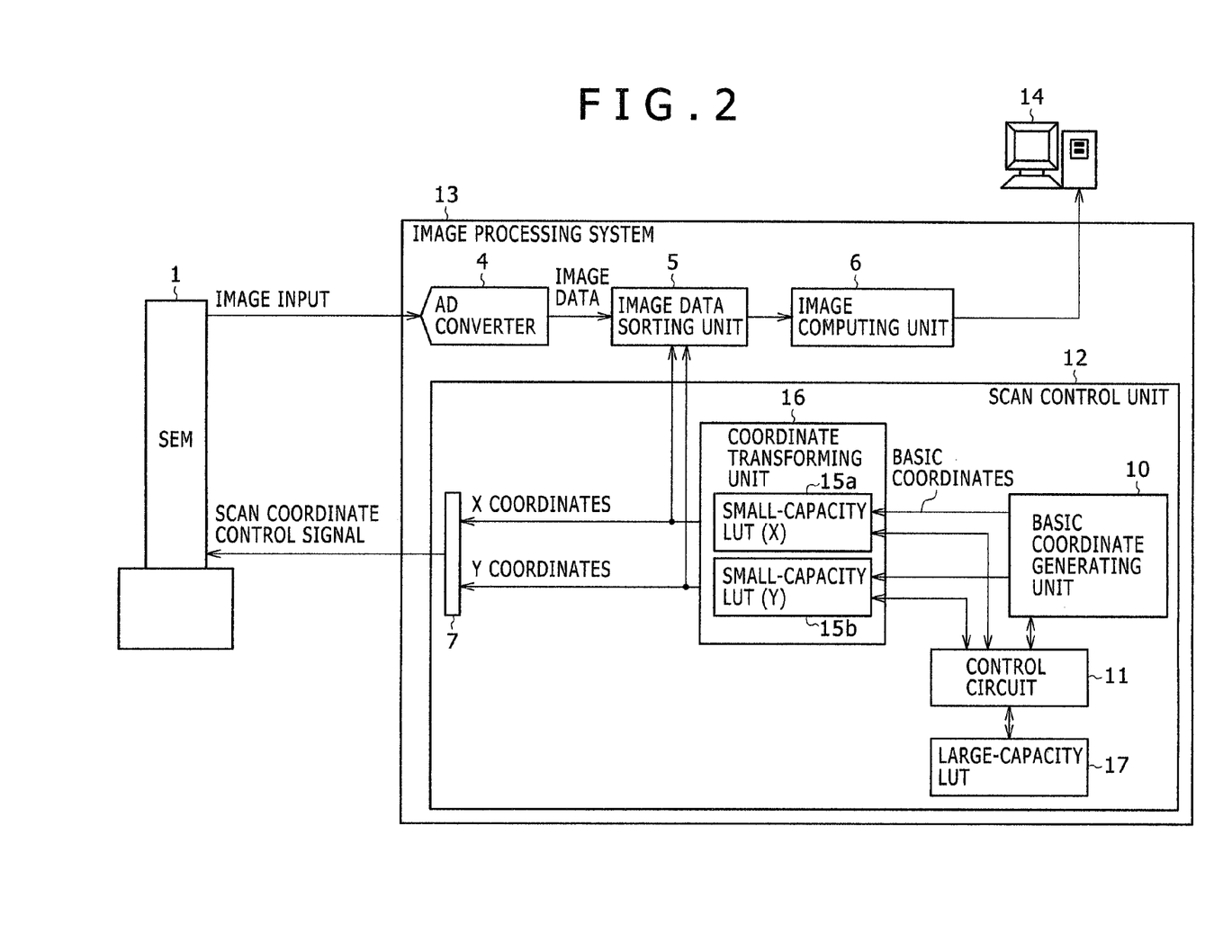
FIG. 2 is a diagram showing the configuration of a first embodiment, using transformation tables (LUT) as a coordinate transforming unit in a scan control unit.

FIG. 2 is a diagram showing the configuration of the first embodiment. In the embodiment, as the X-coordinate transforming unit 8 and the Y-coordinate transforming unit 9 shown in FIG. 1, small-capacity transformation tables (LUTs) 15*a* and 15*b* for transformation to X and Y scan coordinates at high speed and a large-capacity transformation table (LUT) 17 having a capacity of plural image sizes and storing transformed data by scan types so as to be adapted to plural scan types are used. The X and Y coordinates are transformed by pre-storing data to be transformed in the transformation tables (LUTs). The transformation tables (LUTs) are a memory (storing unit). The transform data is stored in the memory. The basic coordinates generated by the basic coordinate generating unit 10 are used as an address in the memory. By reading data stored in the address, coordinate transformation is performed and X·Y scan coordinates are obtained. It should be noted that the image generating unit 2 and the electronic beam control unit 3 are not shown in FIG. 2.

The capacity of the small-capacity transformation tables (LUTs) 15*a* and 15*b* is related to the image size. For example, in the case where the image size is 512×512, each of the X and Y coordinates is made of nine bits. It is sufficient for the transformation table to have two sets of capacities each made of 9 bits×2^9 depth=9 bits×512=4,608 bits. Similarly, in the case where the image size is 4,096×4,096, each of the X and Y coordinates is made of 12 bits. It is sufficient for the transformation table to have two sets of capacities each made of 12 bits×2^12 depth=49,152 bits (49 Kbits). Also in the case where each of the X and Y coordinates is made of 16 bits in order to be adapted to increase in the image size in future (the image size is 65,536×65,536), it is sufficient for the transformation table to have two sets of capacities each made of 16 bits×2^16 depth=16 bits×65,536=1 Mbit. The capacity can be provided in, for example, an FPGA (Field Programmable Gate Array) or the like.

On the other hand, the large-capacity transformation table (LUT) 17 functions as a storing unit for storing transform data by scan kind in order to be adapted to plural scan types. The capacity of the large-capacity transformation table corresponds to the capacities of the small-capacity transformation tables by scan types. For example, in the case where the number of scan types is 32, the capacity of the small-capacity transformation table when each of the X and Y coordinates is made of 16 bits (the image size of 65,536×65,536) is 1 Mbit. Consequently, two sets of capacities each made of 1 Mbit×32=32 Mbits are sufficient. As a memory having a capacity of 32 Mbits×2=64 Mbits, a memory such as a DRAM can be used.

In the configuration of the embodiment shown in FIG. 2, during scan operation, coordinate transformation is performed at high speed with the small-capacity transformation tables 15*a* and 15*b*. When the scan stops, transform data is transferred from the large-capacity transformation table (LUT) 17 to the small-capacity transformation tables 15*a* and 15*b*.

By using the small-capacity transformation tables (LUTs) 15*a* and 15*b* and the large-capacity transformation table (LUT) 17 as transformation tables and performing coordinate transformation with the small-capacity transformation tables (LUTs) 15*a* and 15*b* during the scan operation, the coordinate transformation can be performed at high speed. For example, in the case where each of the X and Y coordinates is made of 16 bits (up to 65,536×65,536 as image size), an address in a memory as a small-capacity transformation table is made of 16 bits. Consequently, a counter of 16 bits can be used for control of the memory address. In the case of using a single transformation table by combining the transformation tables, memory addresses of 512 bits (=16 bits×32 types) are necessary, and a counter of 512 bits has to be used for control of the memory address. As described above, by reducing the number of bits of a memory address, an access to the memory can be performed at higher speed. Thus, high-speed coordinate transformation can be performed. In addition, as the small-capacity transformation table can be provided for an FPGA (Field Programmable Gate Array) or the like. An external memory is unnecessary and time of an access with an external memory is unnecessary. Thus, high-speed operation can be performed.

With the configuration, a high-speed can control capable of transforming coordinates to arbitrary coordinates by plural scan types can be performed.

Second Embodiment

Figure 3:
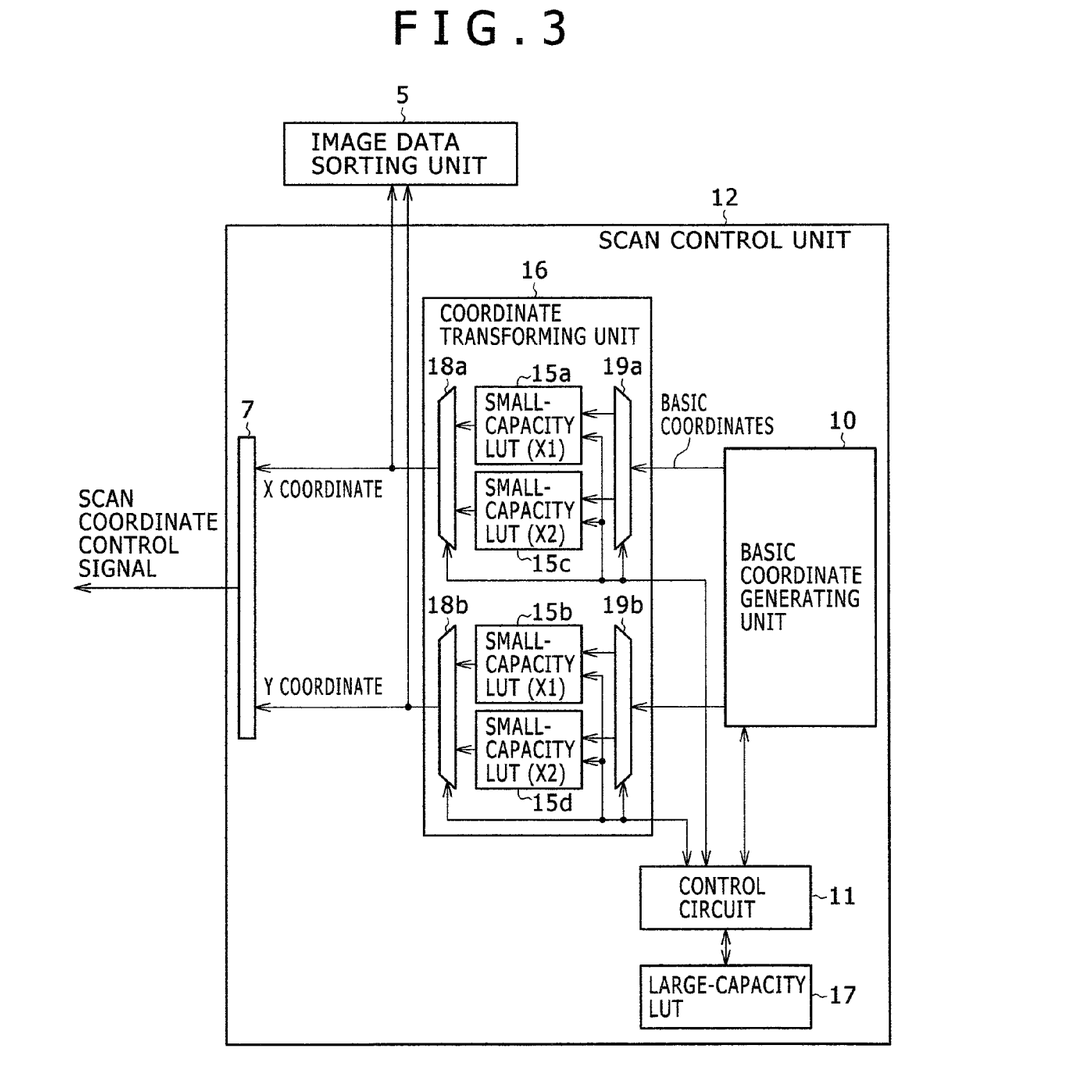
FIG. 3 is a diagram showing the configuration of a scan control unit of a second embodiment, using two transformation tables (LUTs) for an X coordinate and two transformation tables (LUTs) for a Y coordinate in the coordinate transforming unit.

FIG. 3 is a diagram showing the configuration of a second embodiment of the scan control unit in the image processing system. In the second embodiment, a coordinate transforming unit 16 in FIG. 2 has two or more transformation tables (LUTs) for each of the X and Y coordinates. In the configuration, during a scan operation, coordinate transformation is performed with the first small-capacity transformation table (X1 or Y1) 15a or 15b. Simultaneously, transformation data is transferred from the large-capacity transformation table 17 to the second small-capacity transformation table (X2 or Y2) 15c or 15d. After completion of the scan, input/output signals of the first small-capacity transformation table (X1 or Y1) 15a or 15b and those of the second small-capacity transformation table (X2 or Y2) 15c or 15d are switched by switching units 18a, 19a, 18b, and 19b. In such a manner, the two small-capacity transformation tables are alternately used per scan.

With the configuration of the embodiment, by transferring transformation data for the next scan from the large-capacity transformation table to the small-capacity transformation table during a scan operation, transfer time is shortened, and the throughput of the test apparatus can be improved.

Figure 4:
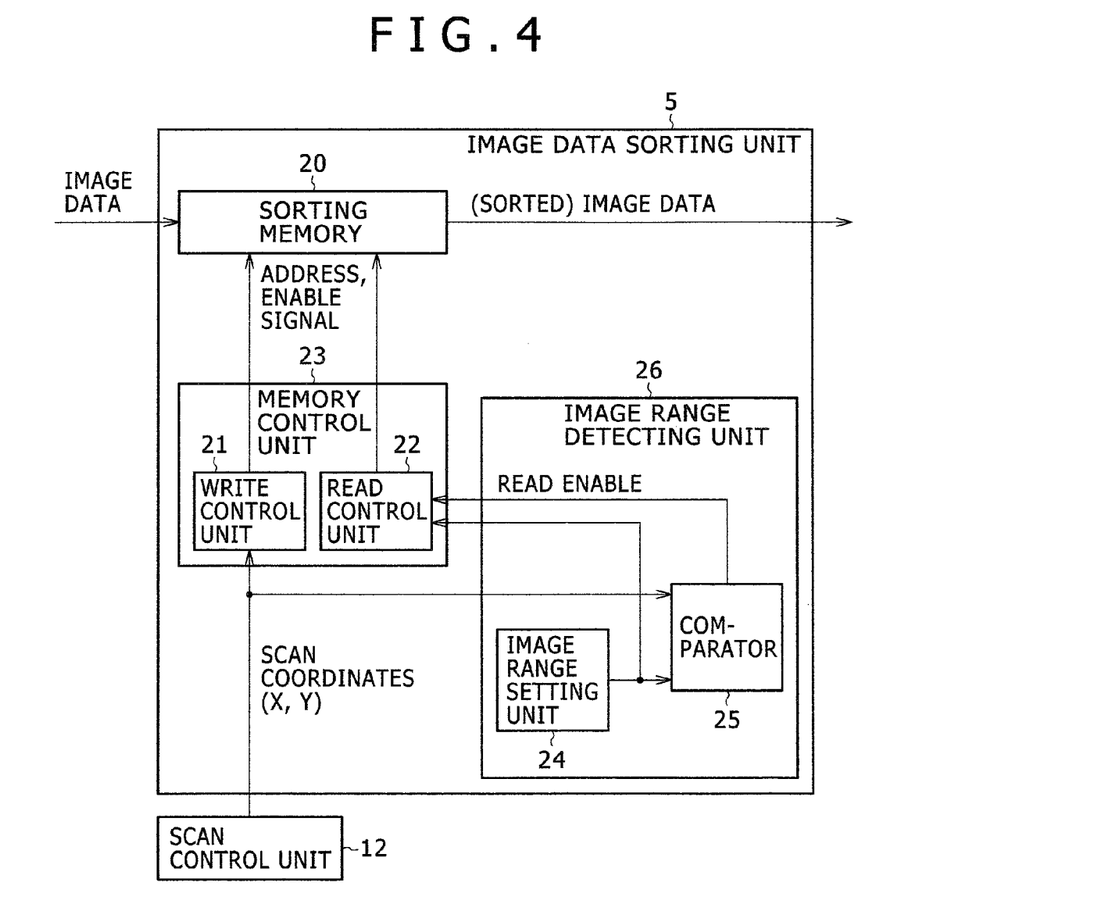
FIG. 4 is a diagram showing the configuration of an example of an image data sorting unit in the configuration of each of the embodiments.

FIG. 4 is a diagram showing the configuration of a concrete example of the image data sorting unit 5 in the image processing system of FIG. 1. The image data sorting unit 5 has a sorting memory 20, a memory control unit 23, and an image range detecting unit 26. The memory control unit 23 is constructed by a write control unit 21 and a read control unit 22. The image range detecting unit 26 is constructed by an image range setting unit 24 and a comparator 25. The image data sorting unit 5 sorts image data scanned in an arbitrary direction in accordance with an order of a normal scan in a predetermined direction on the basis of the X/Y scan coordinates generated by the scan control unit 12 for generating scan coordinates. The write control unit 21 in the memory control unit 23 receives the X/Y scan coordinates generated by the scan control unit 12 and writes the input image data into the sorting memory 20 using the coordinates as an address in the sorting memory 20. The scan coordinates are also input to the image range detecting unit 26 and are compared with an image range which is preset in the image range setting unit 24 by the comparator 25. When the scan coordinates coincide with the image range, a read enable signal and an image range set value are input to the read control unit 22, and the read control unit 22 reads the image data from the sorting memory 20.

As the value stored in the image range setting unit 24, an image range as a unit of performing the image process is set. For example, in the case of performing a 3×3 filter process, if eight pieces of image data around target image data exist, the process can be performed. Therefore, eight coordinates around scan coordinates are stored in the image range setting unit 24. Usually, in the case where a scan is performed in an arbitrary direction, all of image data has to be temporarily stored in an image memory or the like. For example, in the case of an image size of 512×512, the apparatus waits until 262,144 pieces of image data are entered. Due to this, the transfer time since a scan starts until an imaging process is performed is long, and it is difficult to increase the speed. On the other hand, with the configuration of the image data sorting unit 5 of the embodiment, the imaging process can start in the time of entering the unit of performing the imaging process, so that the image data transfer time can be shortened.

Figure 8:
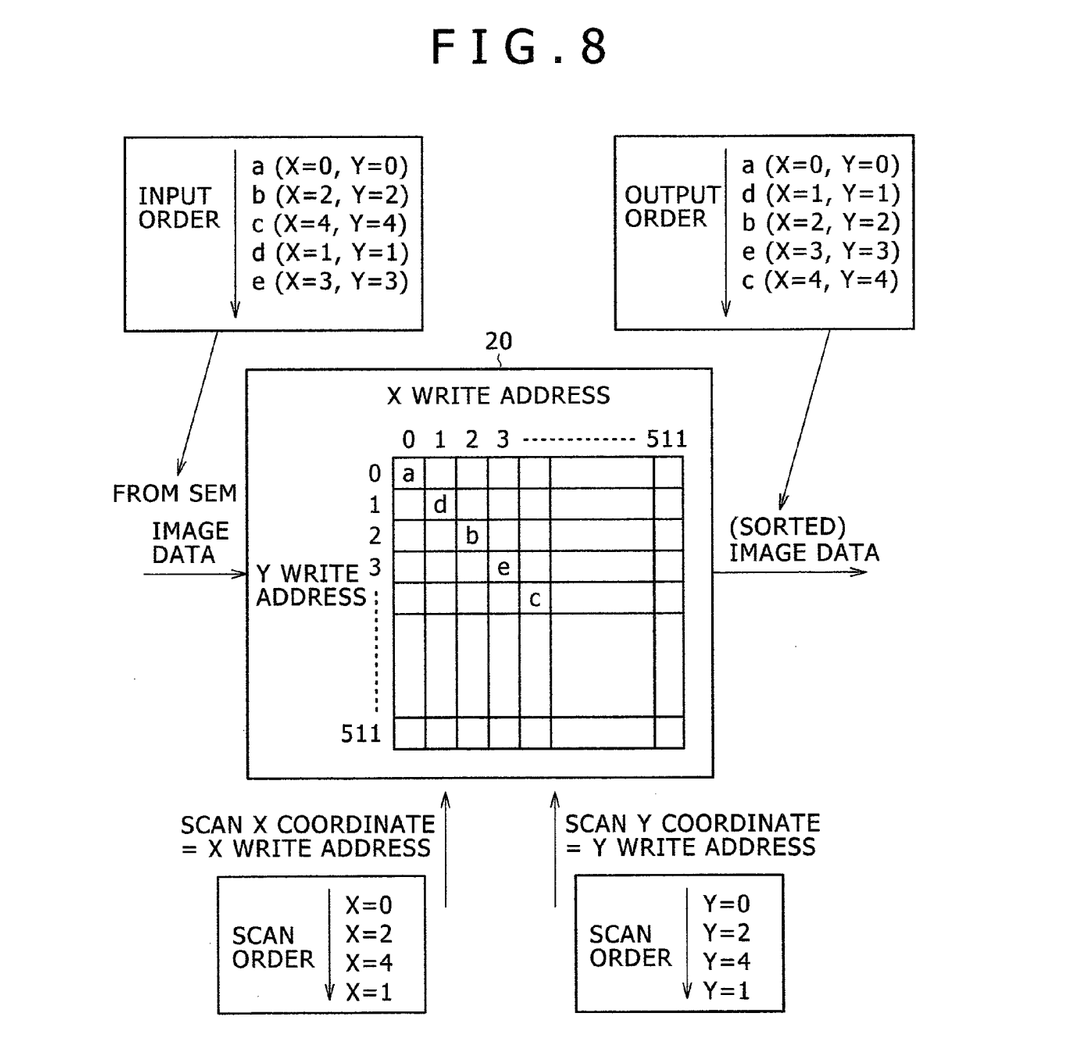
FIG. 8 is a diagram showing outline of operation in an example of the image data sorting unit in FIG. 4.

FIG. 8 is a diagram illustrating outline of the sorting operation in the example of the image data sorting unit 5 using the sorting memory 20 of FIG. 4. The sorting memory 20 is constructed by a two-dimensional map of X and Y write addresses. As described above, in the sorting memory 20, X and Y scan coordinates from the scan control unit 12 are used as X and Y write addresses of the sorting memory, and image data input from the SEM 1 is used as write data of the sorting memory 20. Consequently, in the sorting memory 20, image data from the SEM 1 is written to an address similar to the scan coordinates. After completion of the writing of the image data to the sorting memory 20, by reading the image data in order, sorting is performed. For example, in the case where data in the X coordinates is scanned in the order of 0, 2, 4, 1, 3, . . . and data in the Y coordinates is similarly scanned in the order of 0, 2, 4, 1, 3, . . . , image data from the SEM 1 is input in the order of a (X=0, Y=0), b (X=2, Y=2), c (X=4, Y=4), d (X=1, Y=1), and e (X=3, Y=3). By writing the image data to the sorting memory 20 using the X and Y scan coordinates as a write address and reading the image data in order of 0, 1, 2, 3, 4, . . . in the X and Y addresses, the image data can be sorted to the order of a normal scan in a predetermined direction.

With the configuration of the embodiment of the image data sorting unit 5 described above, even in the case of using image data scanned in an arbitrary direction, by transferring the image data to the image computing unit 6 per range of performing the image computation, high-speed transfer can be performed.

Figure 5A:
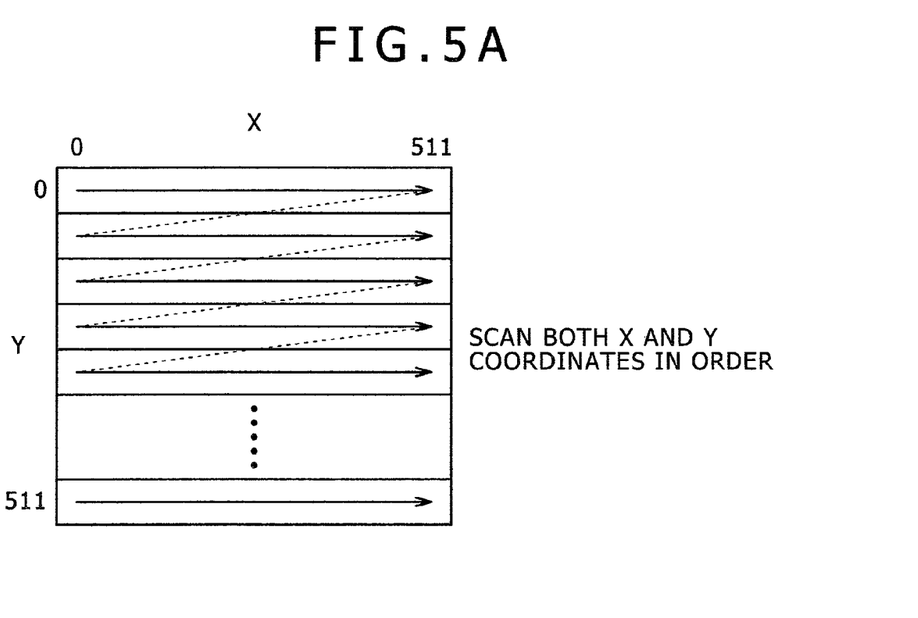
FIG. 5A is a diagram showing outline of an interlace scan as one of scan modes in each of the embodiments.
Figure 5B:
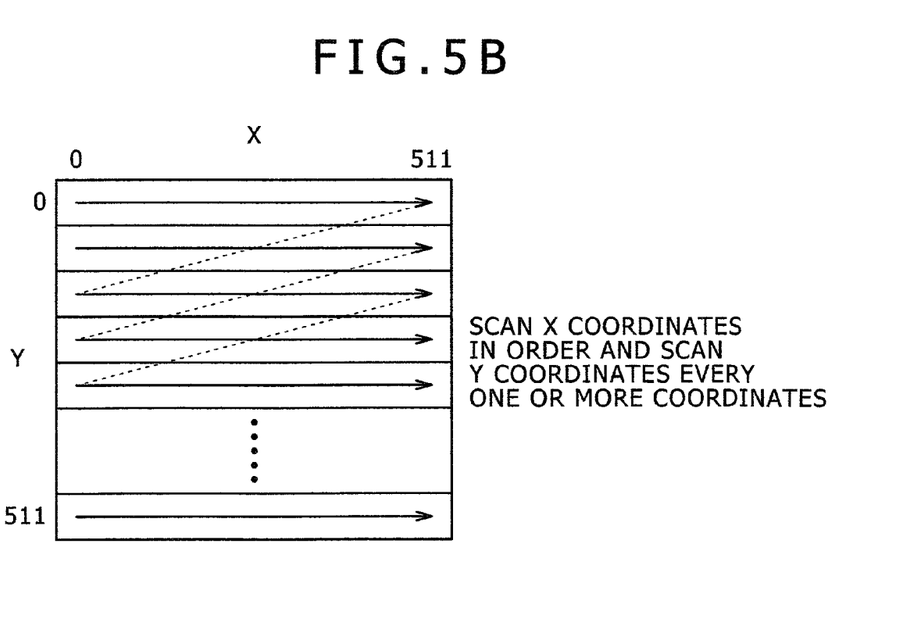
FIG. 5B is a diagram showing outline of a non-interlace scan as one of the scan modes in each of the embodiments.
Figure 5C:
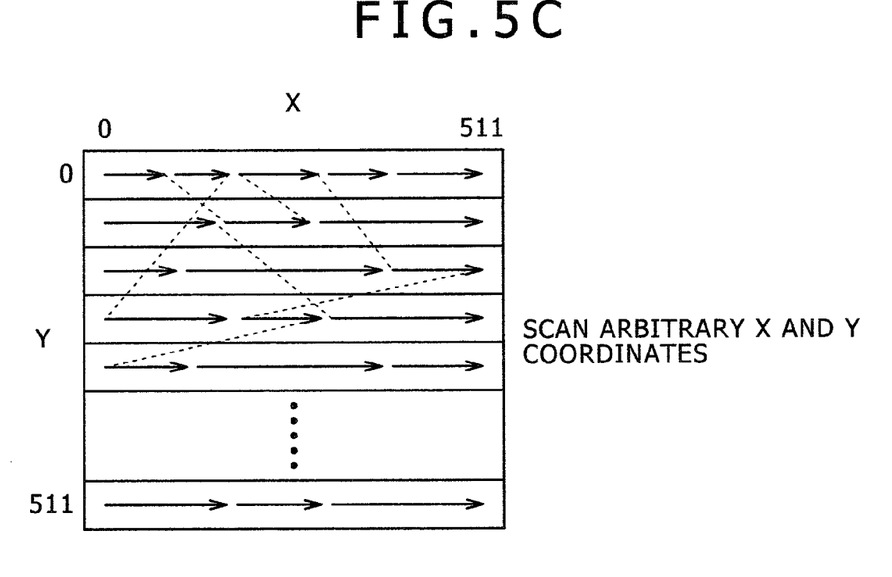
FIG. 5C is a diagram showing outline of a flat scan as a scan mode which is enabled in each of the embodiments.

FIGS. 5A, 5B, and 5C show outline of various scans executed in the above-described embodiments. In a non-interlace scan of FIG. 5A, data is scanned in order in both of the X and Y coordinates. In an interlace scan of FIG. 5B, data in the X coordinates is scanned in order, and data in the Y coordinates is scanned every one or more coordinates. In the configuration of the embodiments, the scan control unit 12 can perform coordinate transformation in each of the X and Y coordinates. Therefore, data in arbitrary coordinates can be scanned as shown in FIG. 5C. Although a scan of data in arbitrary coordinates is shown in FIG. 5C, obviously, this is a mode of the flat scan of scanning data in an arbitrary direction, and the flat scan is not limited to the case of scanning data in arbitrary coordinates.

Figure 6A:
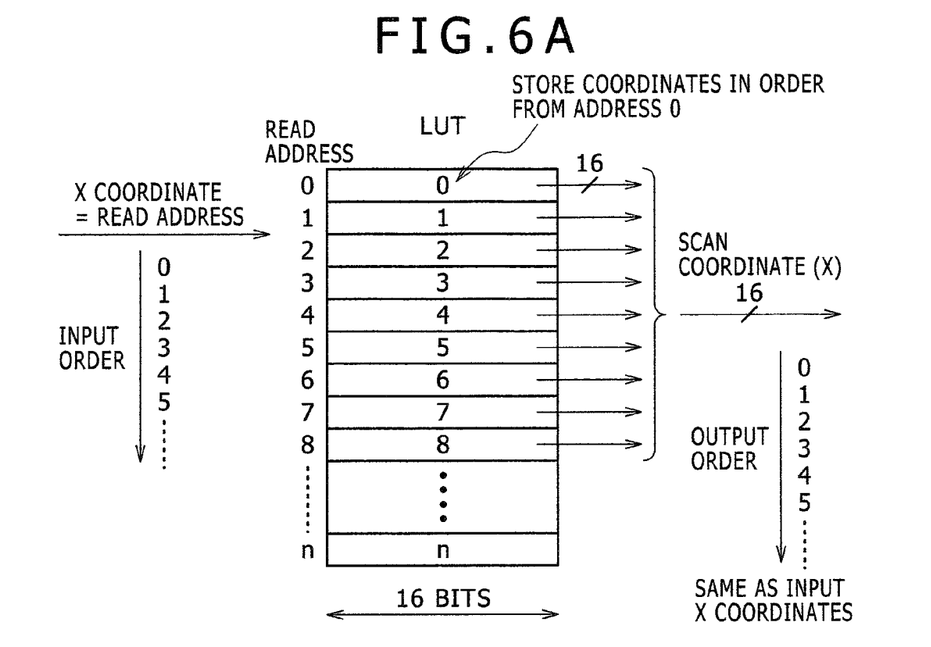
FIG. 6A is a diagram showing storage to a transformation table (LUT) in the interlace scan as one of the scan modes in the embodiments.
Figure 6B:
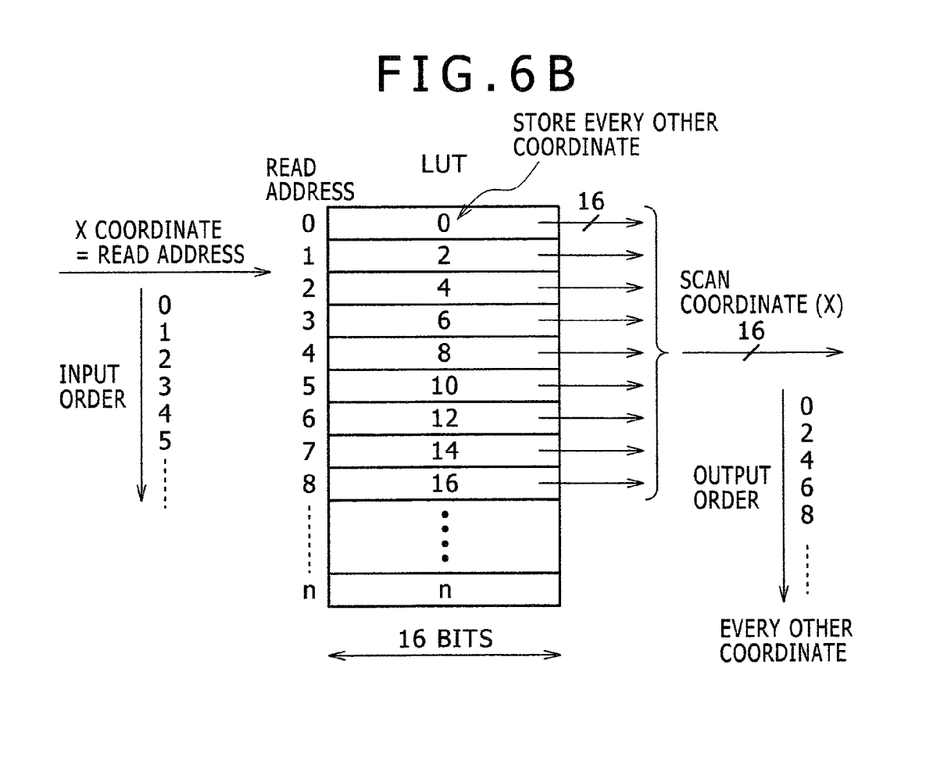
FIG. 6B is a diagram showing storage to a transformation table (LUT) in a non-interlace scan as one of the scan modes in the embodiments.
Figure 6C:
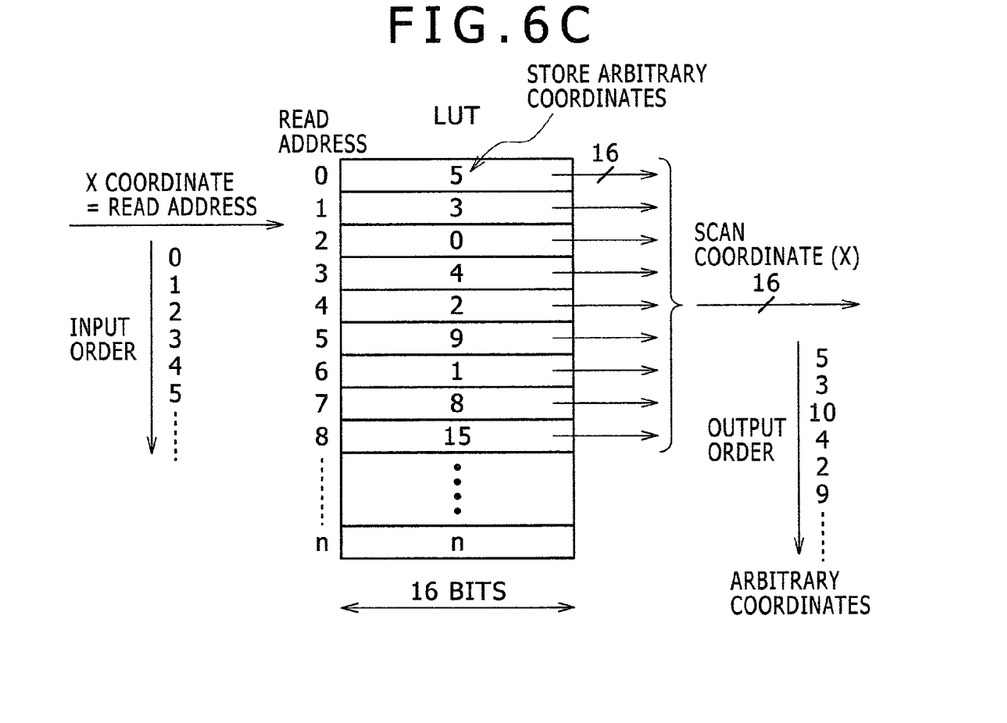
FIG. 6C is a diagram showing storage to a transformation table (LUT) in the flat scan as a scan mode which is enabled in each of the embodiments.

FIGS. 6A, 6B, and 6C are diagrams corresponding to the scans of FIGS. 5A, 5B, and 5C, respectively and showing storage to the transformation table (LUT) of the coordinate transforming unit 16 in each of the embodiments. Data to be transformed is pre-stored in the transformation table. By using the basic coordinates input from the basic coordinate generating unit 10 as a read address and reading data corresponding to the address, coordinate transformation is performed. Also in the case of the non-interlace scan and the interlace scan as normal scans, by pre-storing coordinate data in the transformation table, the same configuration can be used in all of the cases including an arbitrary scan. As obviously understood from FIGS. 6A, 6B, and 6C, coordinates stored in the transformation tables (LUT) correspond to the non-interlace scan, the interlace scan, and the flat scan, respectively.

With the configuration enabling even image data scanned in an arbitrary direction (flat scan) shown in FIG. 5C to be transferred at high speed by transferring the image data to the image computing unit 6 per image computation range and with the configuration of performing the same coordinate transformation in all of the cases including an arbitrary scan, the test apparatus can switch a scan mode to a mode of a scan in an arbitrary mode in accordance with the charging characteristic of a sample. In this case as well, deterioration in a mode of a normal scan in a predetermined direction and throughput of image acquisition can be prevented.

Figure 7:
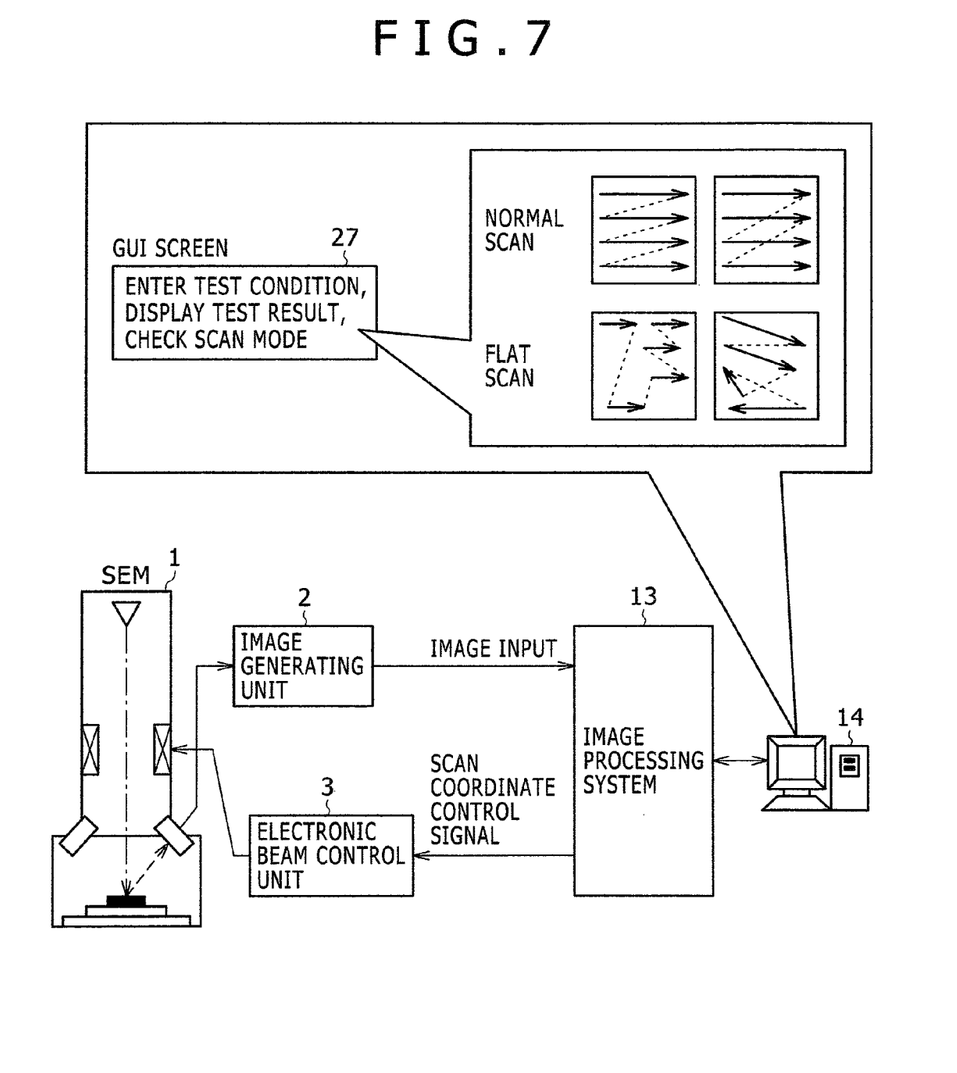
FIG. 7 is a diagram showing outline of a GUI screen in a test apparatus in each of the embodiments.

FIG. 7 is a diagram showing outline of a GUI (Graphic User Interface) screen displayed on the display unit (display) of the overall control unit 14 in each of the embodiments of the test apparatus using an electron beam. The test apparatus in the embodiment has a mode (normal scan mode) of acquiring an image while performing a scan with an electron beam always in a predetermined direction and a mode of acquiring an image while performing an scan with an electron beam in an arbitrary direction (flat scan mode). The image acquisition mode, that is, the scan mode is switched according to the charging characteristic of a sample, and the scan mode is confirmed on the GUI screen 27 displayed on the display unit of the overall control unit 14. As described earlier, the overall control unit 14 is constructed by a PC or the like so that, obviously, the GUI screen on the display unit can be controlled by a program operated by a central processing unit (hereinbelow abbreviated as CPU) on the inside.

For example, at the time of testing a predetermined area to be tested in a semiconductor integrated circuit, the user uses the GUI screen in the test apparatus and sets the mode of performing a scan in an arbitrary direction (flat scan), thereby suppressing the influence of charging on the semiconductor integrated circuit, reducing a distortion in an acquired image, and capable of improving precision of a test.

The test apparatus of the present invention has been described by the SEM using an electron beam as an example. Obviously, the invention can also be applied to test apparatuses using other charged particle beams such as an ion beam.

According to the present invention, by performing a high-speed scan control which is compatible with plural scan types and can transform coordinates to arbitrary coordinates, the charging control can be performed and a semiconductor integrated circuit can be tested at high speed.

According to the present invention, preferably, by alternately using two or more small-capacity transformation tables (LUTs) per scan and transferring transformation data for the next scan from a large-capacity transformation table to the small-capacity transformation table during scanning operation, transfer time is shortened and, as a result, the throughput of the test apparatus can be improved.

More preferably, according to the present invention, by transferring data to the image computing unit per image computation range in the image data sorting unit, high-speed sorting and transfer is performed. Thus, the throughput of the test apparatus can be improved.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. An apparatus for obtaining image information of an area to be tested by irradiating a sample with an electron beam while performing a scan along a plurality of lines using a scanning electronic microscope for emitting an electron beam to a sample, detecting secondary electrons released from the sample, transforming a detection signal to an image signal, displaying the image signal on a screen, and observing the sample, wherein a two-dimensional coordinate generating unit for performing a scan with the electron beam is constructed by a coordinate transforming unit for transforming coordinates in each of a horizontal (X) direction and a vertical (Y) direction, and the area to be tested is scanned with the electron beam in an arbitrary direction.

2. The apparatus according to claim 1, wherein the coordinate transforming unit for transforming coordinates in each of the horizontal (X) direction and the vertical (Y) direction is constructed by a transformation table (LUT) for transforming X and Y coordinates as a reference to arbitrary scan coordinates.

3. The apparatus according to claim 2, further comprising a sorting unit that sorts image data scanned in an arbitrary direction to an order of a scan in a normal predetermined direction on the basis of the scan coordinates generated by the coordinate generating unit, the sorting unit has a sorting memory having a capacity equal to a capacity of image data in the area to be tested, a memory control unit for writing data to the sorting memory using the scan coordinates as a memory address, and an image range detecting unit for detecting an image computation range from the scan coordinates, and the sorting unit transfers the image data per image computation range, thereby performing high-speed sorting and transfer.

4. The apparatus according to claim 1, wherein the coordinate transforming unit is constructed by a small-capacity transformation table (LUT) having a capacity equivalent to image size and transforming the X and Y coordinates as a reference to X and Y scan coordinates, the coordinate generating unit has a large-capacity transformation table (LUT) that stores transformation data by scan types to address a plurality of scan types and has a capacity equal to a plurality of image sizes, during a scan operation, coordinate transformation is performed at high speed using the small-capacity transformation table and, during a scan stops, the transformation data is transferred from the large-capacity transformation table (LUT) to the small-capacity transformation table (LUT).

5. The apparatus according to claim 1, wherein the coordinate transforming unit is constructed by two or more first small-capacity transformation tables (LUTs) and two or more second small-capacity transformation tables (LUTs) each transforming X and Y coordinates as a reference to X and Y scan coordinates, the coordinate generating unit has a large-capacity transformation table (LUT) that stores transformation data by scan types to address a plurality of scan types and has a capacity equal to a plurality of image sizes, during a scan operation, coordinate transformation is performed with the first small-capacity transformation tables (LUTs) and the transformation data is transferred from the large-capacity transformation table (LUT) to the second small-capacity transformation tables (LUTs) and, after completion of the scan, input/output signals of the first small-capacity transformation tables (LUTs) and input/output signals of the second small-capacity transformation tables are switched, and the two or more small-capacity transformation tables (LUT) are alternately used per scan.

6. The apparatus according to claim 1, comprising a mode of acquiring an image while performing a scan with the electron beam always in a predetermined direction and a mode of acquiring an image while performing a scan with the electron beam in an arbitrary direction,
    wherein the image acquisition modes are switched according to a charging characteristic of the sample.

7. The apparatus according to claim 6, further comprising a display unit for displaying a GUI screen,
    wherein the image acquisition modes are switched according to the charging characteristic of the sample on the GUI screen, and the image acquisition mode is confirmed.

8. An apparatus using an electron beam, comprising:
a scanning electron microscope for scanning a sample with the electron beam and detecting secondary electrons released from the sample;
an image processing system for generating a scan coordinate control signal to be applied to the scanning electron microscope to perform a scan with the electron beam, and processing image data in an area to be tested in the sample, which is obtained by detecting the secondary electrons; and
a display unit for displaying a result of the process on the image data in the image processing system,
wherein the image processing system has a coordinate generating unit including a coordinate transforming unit for transforming basic coordinates to scan coordinates in each of a horizontal (X) direction and a vertical (Y) direction in order to generate the scan coordinate control signal, and
the area to be tested is scanned with the electron beam in an arbitrary direction.

9. The apparatus according to claim 8, wherein the coordinate transforming unit is a transformation table (LUT) for transforming the basic coordinates to the scan coordinates in each of the horizontal (X) direction and the vertical (Y) direction.

10. The apparatus according to claim 8, wherein the coordinate transforming unit has a small-capacity transformation table (LUT) for transforming the basic coordinates to the scan coordinates in each of the horizontal (X) direction and the vertical (Y) direction and corresponding to the area to be tested,
    the coordinate generating unit has a large-capacity transformation table (LUT) for storing coordinate transformation data by a plurality of scan types,
    during a scan operation, coordinate transformation is performed with the small-capacity transformation table and,
    during a scan stops, the coordinate transformation data is transferred from the large-capacity transformation table (LUT) to the small-capacity transformation table (LUT).

11. The apparatus according to claim 8, wherein the coordinate transforming unit has two or more first small-capacity transformation tables (LUTs) and two or more second small-capacity transformation tables (LUTs) each transforming the basic coordinates to the scan coordinates in each of a horizontal (X) direction and a vertical (Y) direction and corresponding to the area to be tested,
    the coordinate generating unit has a large-capacity transformation table (LUT) that stores coordinate transformation data by a plurality of scan types,
    during a scan operation, coordinate transformation is performed with the first small-capacity transformation tables (LUTs) and, simultaneously, the coordinate transformation data is transferred from the large-capacity transformation table (LUT) to the second small-capacity transformation tables (LUTs) and,
    after completion of the scan, the first small-capacity transformation tables (LUTs) and the second small-capacity transformation tables are switched, and
    the two or more small-capacity transformation tables (LUTs) are switched and used per scan.

12. The apparatus according to claim 8, wherein the image processing system has an image data sorting unit to which image data is input, and
    the image data sorting unit sorts the image data obtained by a scan with the electron beam in an arbitrary direction to an order of a scan in a predetermined direction on the basis of the scan coordinates output from the coordinate transforming unit.

13. The apparatus according to claim 12, wherein the image processing system has an image computing unit to which image data output from the image data sorting unit is input and which performs image computation on the image data output,
    the image data sorting unit has a sorting memory having a capacity equal to a capacity of the image data in the area to be tested, a memory control unit for writing data to the sorting memory using the scan coordinates as a memory address, and an image range detecting unit for detecting an image computation range by the image computing unit on the basis of the scan coordinates, and
    the image data is transferred to the image computing unit per image computation range by the image computing unit.

14. A test apparatus using an electron beam, comprising:
a scanning electron microscope for scanning a sample with the electron beam and detecting secondary electrons released from the sample;
an image processing system for generating a control signal for performing a two-dimensional scan with the electron beam, to be applied to the scanning electron microscope, and processing image data in an area to be tested in the sample, obtained by detecting the secondary electrons; and
a display unit for displaying a result of the process on the image data in the image processing system,
wherein the image processing system has a coordinate generating unit for generating scan coordinates in each of a horizontal (X) direction and a vertical (Y) direction, and
the coordinate generating unit has a transformation table having a capacity corresponding to the area to be tested and transforming basic coordinates to the scan coordinates in each of the horizontal (X) direction and the vertical (Y) direction, and a storing unit for storing coordinate transformation data by a plurality of scan types.

15. The apparatus according to claim 14, wherein the image processing system has an image data sorting unit to which the image data is input, and the image data sorting unit sorts the image data obtained by performing a scan with the electron beam in an arbitrary direction to an order of a scan in a predetermined direction on the basis of the scan coordinates output from the coordinate generating unit.

\* \* \* \* \*